US009961898B2

(12) United States Patent
Meador et al.

(10) Patent No.: US 9,961,898 B2
(45) Date of Patent: May 8, 2018

(54) METHOD FOR CONTROLLING PLANT DISEASE

(75) Inventors: Christopher B. Meador, Leland, MS (US); Karen S. Arthur, Plano, TX (US)

(73) Assignee: SUMITOMO CHEMICAL COMPANY, LIMITED, Toyko (JP)

(*) Notice: Subject to any disclaimer, the term of this patent is extended or adjusted under 35 U.S.C. 154(b) by 0 days. days.

(21) Appl. No.: 13/062,766

(22) PCT Filed: Sep. 11, 2009

(86) PCT No.: PCT/US2009/056591
§ 371 (c)(1),
(2), (4) Date: May 3, 2011

(87) PCT Pub. No.: WO2010/030833
PCT Pub. Date: Mar. 18, 2010

(65) Prior Publication Data
US 2011/0201660 A1 Aug. 18, 2011

Related U.S. Application Data

(60) Provisional application No. 61/096,438, filed on Sep. 12, 2008.

(51) Int. Cl.
A01N 43/78 (2006.01)
A01N 25/00 (2006.01)

(52) U.S. Cl.
CPC .................. A01N 43/78 (2013.01)

(58) Field of Classification Search
None
See application file for complete search history.

(56) References Cited

U.S. PATENT DOCUMENTS

| | | | |
|---|---|---|---|
| 6,551,962 B1* | 4/2003 | Pershing et al. | 504/100 |
| 6,593,299 B1* | 7/2003 | Bennett et al. | 424/408 |
| 6,740,671 B2* | 5/2004 | Kang et al. | 514/370 |
| 7,897,846 B2* | 3/2011 | Chicoine | A01H 5/10 800/288 |
| 7,982,106 B1* | 7/2011 | Chang et al. | 800/320.1 |
| 8,124,564 B2* | 2/2012 | Rochling et al. | 504/100 |
| 8,426,605 B2* | 4/2013 | Andersch et al. | 548/182 |
| 2003/0203949 A1 | 10/2003 | Kang et al. | |
| 2006/0242732 A1* | 10/2006 | Carozzi et al. | 800/279 |
| 2007/0093391 A1 | 4/2007 | Fischer et al. | |
| 2007/0298966 A1 | 12/2007 | Fischer et al. | |
| 2008/0200334 A1* | 8/2008 | Tormo I Blasco | A01N 43/78 504/100 |
| 2008/0269051 A1 | 10/2008 | Suty-Heinze et al. | |
| 2009/0286681 A1 | 11/2009 | Dahmen et al. | |
| 2011/0152097 A1 | 6/2011 | Stenzel et al. | |

FOREIGN PATENT DOCUMENTS

| | | |
|---|---|---|
| CL | 2005-3050 | 11/2005 |
| CN | 1835954 | 9/2006 |
| DE | 10 2005 026 482 A1 | 12/2006 |
| EP | 0353191 | 1/1990 |
| EP | 0374753 | 6/1990 |
| EP | 0392225 | 10/1990 |
| EP | 0427529 | 5/1991 |
| EP | 0451878 | 10/1991 |
| JP | 2003-532653 A | 11/2003 |
| JP | 2008-515830 A | 5/2008 |
| JP | 2008-515949 A | 5/2008 |
| KR | 10-2001-0103501 | 11/2001 |
| WO | WO 1993/007278 | 4/1993 |
| WO | WO 1995/033818 | 12/1995 |
| WO | WO 1995/034656 | 12/1995 |
| WO | 2001084930 A1 | 11/2001 |
| WO | WO 2003/000906 | 1/2003 |
| WO | WO 2003/052073 | 6/2003 |
| WO | WO 2006/131230 | 12/2006 |
| WO | WO 2007/031141 A1 | 3/2007 |
| WO | WO 2010/046389 | 4/2010 |
| WO | WO 2001/084930 | 11/2011 |

OTHER PUBLICATIONS

Nerling et al, Journal of Seed Science, 2013, vol. 35, No. 4, pp. 449-456.*
Office Action and Search Report corresponding to related Chinese Application No. 200980135812 dated Nov. 19, 2012.
Examination Report corresponding to related New Zealand Application No. 591304 dated Jul. 22, 2011.
Office Action corresponding to related Ukrainian Application No. 201104453 dated Dec. 14, 2012.
Extended European Search Report dated May 23, 2013.
Kim et al., "Synthesis and fungicidal activity of ethaboxam oomysetes" Bognor Regis; GB, vol. 60, No. 10, Jan. 1, 2004 pp. 1007-1012, XP002332654.
Kim et al. "Synthesis and fungicidal activity of ethaboxam against Oomycetes", Pest Management Science, 60:1007-1012 (online: 2004).
Office Action issued in corresponding Taiwanese application No. 098128161 dated Aug. 26, 2014.

(Continued)

Primary Examiner — Eileen B O Hara
(74) Attorney, Agent, or Firm — Wood, Phillips, Katz, Clark & Mortimer

(57) ABSTRACT

The combination of ethaboxam and transgenic plants provides enhanced plant protection in controlling plant disease. According to the present invention, an application of an effective amount of ethaboxam to transgenic plants applied to plant foliage parts; soil-applied in drench or soil incorporation; or applied to seed using seed slurry application, seed film coating and seed pelleting technologies for seed, gives a good controlling effect on plant diseases. Application of ethaboxam to transgenic plants encompasses all monocotyledonous and dicotyledonous crop types.

9 Claims, No Drawings

(56) References Cited

OTHER PUBLICATIONS

Office Action issued in corresponding Philippine application No. 1/2011/500398 dated Oct. 9, 2014.
Office Action issued in corresponding Australian application No. 2009291671 dated Jul. 31, 2014.
Office Action issued in corresponding Japanese application No. 2011-526982 dated Aug. 4, 2014—with English translation.
Office Action issued in corresponding Philippine application No. 1/2011/500398 dated Jun. 9, 2014.
Office Action issued in corresponding Taiwanese application dated Apr. 9, 2014, Application 098128161.
Office Action issued in corresponding Columbian application dated Mar. 31, 2014, Application 11030024.
Office Action issued in corresponding Korean application 2011-7005621 dated Jan. 15, 2016.
Office Action issued in corresponding Chinese application 200980135812.4 dated Aug. 2, 2013 (Previously submitted to the USPTO Sep. 10, 2013).
Office Action issued in corresponding Russian application 2011114132/13(020895) dated Jun. 6, 2013 (Previously submitted to the USPTO Sep. 10, 2013).
Office Action issued in corresponding Japanese application 2011-526982 dated Dec. 9, 2013 (Previously submitted to the USPTO Jan. 24, 2014).
Office Action issued in corresponding European application 09 813 642.7-1454 dated Feb. 24, 2014 (Previously submitted to the USPTO Mar. 20, 2014).
Office Action issued in corresponding Chilean application 521-2011 (2011-000521) dated Oct. 2, 2015.
Office Action issued in corresponding Canadian application 2,736,121 dated Aug. 10, 2015.
Office Action issued in corresponding Taiwanese application 098128161 dated Jul. 27, 2015.
Patent Examination Report No. 1 dated Jun. 11, 2015 for corresponding Australian Patent Application No. 2015201870.
Subsequent Substantive Examination Report dated Jun. 9, 2015 for corresponding Philippines Patent Application No. 1-2011-500398.
Kim et al. "Synthesis and fungicidal activity of ethaboxam against Oomycetes", Pest Management Science, 2004, vol. 60, No. 10, pp. 1007-1012.
Office Action issued in corresponding Japanese application 2011-526982 dated Dec. 17, 2013 (Previously submitted to the USPTO Jan. 24, 2014).
Office Action issued in corresponding Brazilian application PI0918248-9 dated Nov. 22, 2016.
Office Action issued in corresponding Chilean application 2011-00521 dated Sep. 22, 2016.
Office Action issued in correspondence Korean application 2016-7024794 dated Sep. 23, 2016.
Office Action issued in corresponding Philippine application 1/2011/500398 dated Oct. 28, 2016.
Office Action issued in corresponding Canadian application 2,736,121 dated May 16, 2016.
Office Action issued in corresponding Philippine application 1-2011-500398 dated Mar. 29, 2017.
Office Action issued in corresponding India application 1657/CHENP/2011 dated Apr. 5, 2017.
Substantive Examination Adverse Report issued in corresponding Malaysian application PI 2011000796 dated Mar. 15, 2016.
Office Action issued in corresponding Chilean application 2011-000521 dated Dec. 15, 2014.
Rejection Decision issued in corresponding Brazilian Application No. PI0918248-9 dated Jun. 20, 2017.

\* cited by examiner

METHOD FOR CONTROLLING PLANT DISEASE

FIELD OF THE INVENTION

The present invention is directed to a method for controlling plant disease.

BACKGROUND ART

N-(cyano-2-thienylmethyl)-4-ethyl-2-(ethylamino)-5-thiazolecarboxamide (ethaboxam) is known as an active ingredient of fungicide in U.S. Pat. No. 6,740,671.

SUMMARY OF THE INVENTION

The present invention provides a method for controlling plant disease. It is characterized by the combination of ethaboxam and transgenic plants. According to the present invention, an application of an effective amount of ethaboxam to transgenic plants provides improved plant stand establishment demonstrating good controlling effect against plant diseases.

DETAILED DESCRIPTION OF THE INVENTION

Ethaboxam can be prepared by the method disclosed in U.S. Pat. No. 6,740,671, which is incorporated herein by reference and it is also available on the market.

In the present invention, transgenic plants are defined as plants transformed by means of recombinant DNA technology. The transgenic plants may contain one or more genes expressing a pesticidal protein, which provide plant protection against insects, and other biological pests of plants. The plants may be tolerant against pesticides, especially certain type of herbicides. They may be resistant against the attack of fungi, bacteria or virus. Further, they may have resistance against plant stress that is a beneficial feature in agriculture, or the transgenic plants may provide a beneficial feature such as high crop yield, enhanced quality, long-term storage period and other useful properties.

Examples of transgenic plants include plants which are tolerant against herbicides such as HPPD inhibitor (e.g., isoxaflutole), ALS inhibitor (e.g., imazethapyr, thifensulfuron-methyl), EPSP syntase inhibitor, glutamine syntase inhibitor, bromoxynil and synthetic auxin (dicamba); plants which contain one or more genes expressing a pesticidally active ingredient (e.g., toxins from *Bacillus* spp.); and plants which can produce an antimicrobial substance. The transgenic plants may have two or more features mentioned above.

Typical examples of herbicide-tolerant plants include corn, soybean, cotton and canola having tolerance against glyphosate or glufosinate. Roundup Ready (trademark of Monsanto), RoundupReady 2 (trademark of Monsanto) and LibertyLink (trademark of Bayer Crop Science) are glyphosate or glufosinate products that are commercially available. Examples of toxins expressed in the transgenic plants include *Bacillus cereus* proteins and *Bacillus popliae* proteins; *Bacillus thuringiensis* endotoxins (e.g., Cry1Ab, Cry1Ac, Cry1F, Cry1Fa2, Cry2Ab, Cry3a, Cry3Bb1, Cry9C), VIP1, VIP2, VIP3 and VIP3A; insecticidal proteins originated from nematode; toxins originated from animals such as scorpion venom, spider venom, wasp venom and neurotoxins which are specific to insects; fungul toxins; agglutinin such as plant lectin; protease inhibitors such as trypsin inhibitors, serine protease inhibitors, patatin, cystatin and papain inhibitors; ribosome inactivating protein (RIP) such as ricin, corn-RIP, abrin, rufin, saporin and briodin; steroid metabolic enzyme such as 3-hydroxysteroid oxidase, ecdysteroid-UDP-glucosyltransferase and cholesterol oxidase; ecdysone inhibitors; HMG-COA reductase; ion channel inhibitors such as sodium channel inhibitor and calcium channel inhibitor; juvenile hormone esterase; diuretic hormone receptors; stilbene syntase; bibenzyl syntase; chitinase; and glucanase.

The toxins expressed in the transgenic plants include hybrid toxins of insecticidal proteins such as δ-endotoxin proteins (e.g., Cry1Ab, Cry1Ac, Cry1F, Cry1Fa2, Cry2Ab, Cry3a, Cry3Bb1, Cry9C), VIP1, VIP2, VIP3 and VIP3A; toxins partially lacking amino acids; and modified toxins. The hybrid toxins can be produced by combining different domains of the proteins by means of recombinant technology. With regard to the toxins partially lacking amino acids, Cry1Ab lacking a part of amino acid sequence is known. In the modified toxins, one or more amino acids of naturally occurring toxins are substituted by the other amino acids.

Examples of the toxins and plants which express toxins are described in many published patent applications such as EP-0374753A, EP-0427529A, EP-0451878A, WO 93/07278, WO 95/34656 and WO 03/52073.

The toxins in the transgenic plants, particularly, give resistance against Coleoptera pests, Diptera pests and Lepidoptera pests to plants.

Typical examples of the transgenic plants producing toxins are Yieldgard (trademark of Monsanto, corn expressing Cry1Ab toxin), Yieldgard Rootworm (trademark of Monsanto, corn expressing Cry3Bb1 toxin), Yieldgard Plus (trademark of Monsanto, corn expressing Cry1Ab and Cry3Bb1 toxins), Herculex I (trademark of Dow AgroSciences, corn expressing Cry1Fa2 toxin and expressing phosphinotricine N-acetyltransferase (PAT) for giving tolerance against glufosinate), NuCOTN33B (cotton expressing Cry1Ac toxin), Bollgard I (trademark of Monsanto, cotton expressing Cry1Ac toxin), Bollgard II (trademark of Monsanto, cotton expressing Cry1Ac and Cry2Ab toxins), VIP-COT (trademark of Syngenta, cotton expressing VIP toxin), Newleaf (trademark of Monsanto, potato expressing Cry3A toxin), Naturegard (trademark of Syngenta), Agrisure GT Advantage (trademark of Syngenta, GA21 glyphosate tolerance) and Agrisure CB Advantage (trademark of Syngenta, Bt11 cornborer resistance (CB)).

Examples of the antimicrobial substances which the transgenic plants produce include PR proteins (cf. EP-392225A). These antimicrobial substances and transgenic plants are described in EP-0353191A, EP-0392225A and WO 95/33818.

Examples of the antimicrobial substances expressed in the transgenic plants include ion channel inhibitors such as sodium channel inhibitor and calcium channel inhibitor (It is known that virus produces KP1, KP4 and KP6 toxins and so on.); stilbene syntase; bibenzyl syntase; chitinase; glucanase; PR proteins, peptide antimicrobials; heterocyclic antimicrobials; protein factor which relates to resistance against plant diseases (plant disease resistance gene, cf. WO 03/00906).

In the present invention, ethaboxam is applied to the above-mentioned transgenic plants including monocotyledon crops such as corn, wheat, barley, rye, rice, sorghum and turf; and dicotyledon crops such as cotton, sugar beet, peanut, potato, sunflower, soybean, alfalfa, canola and vegetables. Further, ethaboxam may be applied to transgenic plants including oat; sugarcane; tobacco; Solanaceae vegetables such as eggplant, tomato, green pepper and pepper; Cucurbitaceae vegetables such as cucumber, pumpkin, zucchini, watermelon, melon and squash; Brassicaceae vegetables such as radish, turnip, horseradish, kohlrabi, Chinese cabbage, cabbage, leaf mustard, broccoli and cauliflower; Asteraceae vegetables such as burdock, crown daisy, artichoke and lettuce; Liliaceae vegetables such as leek, onion, garlic and asparagus; Apiaceae vegetables such as carrot, parsley, celery and parsnip; Chenopodiaceae vegetables such as spinach and chard; Lamiaceae vegetables such as perilla, mint and basil; strawberry; sweet potato; yam; taro; flowers such as petunia, morning glory, carnation, chrysanthemum and rose; foliage plants; turf; fruit trees such as pome fruits (e.g., apple, pear, Japanese pear, Chinese quince and quince), stone fruits (e.g., peach, plum, nectarine, Japanese apricot, cherry, apricot and prune), citrus (e.g., Satsuma orange, orange, lemon, lime and grapefruit), tree nuts (e.g., chestnut, pecan, walnut, hazel, almond, pistachio, cashew and macadamia), berries such as blueberry, cranberry, blackberry and raspberry; grapes; persimmon; olive; loquat; banana; coffee; palm; coco; the other trees such tea, mulberry, flower trees, and landscape trees (e.g., ash, birch, dogwood, eucalyptus, ginkgo, lilac, maple, oak, poplar, Chinese redbud, Formosa sweet gum, sycamore, Japanese zerkova, Japanese thuja, fir, hemlock fir, needle juniper, pine, spruce, yew).

Examples of the plant diseases controlled by the present invention include diseases caused by phytopathogenic fungi (in particular of the classes of Ascomycetes, Deuteromycetes, Oomycetes and Basidiomycetes) such as *Magnaporthe grisea, Cochliobolus miyabeanus, Rhizoctonia solani* and *Gibberella fujikuroi* on rice; *Erysiphe graminis, Fusarium graminearum, F. avenacerum, F. culmorum, Microdochium nivale, Puccinia striiformis, P. graminis, P. recondita, P. hordei, Typhula* sp., *Micronectriella nivalis, Ustilago tritici, U. nuda, Tilletia caries, Pseudocercosporella herpotrichoides, Rhynchosporium secalis, Septoria tritici, Leptosphaeria nodorum* and *Pyrenophora teres* on wheat and barley; *Diaporthe citri, Elsinoe fawcetti, Penicillium digitatum, P. italicum, Phytophthora parasitica* and *Phytophthora citrophthora* on citrus; *Monilinia mali, Valsa ceratosperma, Podosphaera leucotricha, Alternaria alternata* apple pathotype, *Venturia inaequalis, Colletotrichum acutatum* and *Phytophtora cactorum* on apple; *Venturia nashicola, V. pirina, Alternaria alternata* Japanese pear pathotype, *Gymnosporangium haraeanum* and *Phytophthora cactorum* on pear; *Monilinia fructicola, Cladosporium carpophilum* and *Phomopsis* sp. on peach; *Elsinoe ampelina, Glomerella cingulata, Uncinula necator, Phakopsora ampelopsidis, Guignardia bidwellii* and *Plasmopara viticola* on grape; *Gloeosporium kaki, Cercospora kaki* and *Mycosphaerella nawae* on persimmon; *Colletotrichum lagenarium, Sphaerotheca fuliginea, Mycosphaerella melonis, Fusarium oxysporum, Pseudoperonospora cubensis* and *Phytophthora* sp. on Cucurbitales vegetables; *Alternaria solani, Cladosporium fulvum* and *Phytophthora infestans* on tomato; *Phomopsis vexans* and *Erysiphe cichoracearum* on eggplant; *Alternaria japonica, Cercosporella brassicae, Plasmodiophora brassicae* and *Peronospora parasitica* on Brassicaceae vegetables; *Puccinia allii* and *Peronospora destructor* on leek; *Cercospora kikuchii, Elsinoe glycines, Diaporthe phaseolorum* var. *sojae, Phakopsora pachyrhizi* and *Phytophthora sojae* on soybean; *Colletotrichum lindemuthianum* of kidney bean; *Cercospora personata, Cercospora arachidicola* and *Sclerotium rolfsii* on peanut; *Erysiphe pisi* on pea; *Alternaria solani, Phytophthora infestans, Phytophthora erythroseptica* and *Spongospora subterranean f.* sp. *subterranean* on potato; *Sphaerotheca humuli* and *Glomerella cingulata* on strawberry; *Exobasidium reticulatum, Elsinoe leucospila, Pestalotiopsis* sp. and *Colletotrichum theae-sinensis* on tea; *Alternaria longipes, Erysiphe cichoracearum, Colletotrichum tabacum, Peronospora tabacina* and *Phytophthora nicotianae* on tobacco; *Cercospora beticola, Thanatephorus cucumeris*, and *Aphanidermatum cochlioides* on sugar beet; *Diplocarpon rosae, Sphaerotheca pannosa* and *Peronospora sparsa* on rose; *Bremia lactucae, Septoria chrysanthemi-indici* and *Puccinia horiana* on chrysanthemum and Compositae vegetables; *Alternaria brassicicola* on radish; *Sclerotinia homeocarpa* and *Rhizoctonia solani* on turf; *Mycosphaerella fijiensis* and *Mycosphaerella musicola* on banana; *Plasmopara halstedii* on sunflower; and various diseases on crops caused by *Pythium* spp. (e.g., *Pythium aphanidermatum, Pythium debaryanum, Pythium graminicola, Pythium irregulare, Pythium ultimum*), *Botrytis cinerea, Sclerotinia sclerotiorum, Aspergillus* spp., *Penicillium* spp., *Fusarium* spp., *Gibberella* spp., *Trichoderma* spp., *Thielaviopsis* spp., *Rhizopus* spp., *Mucor* spp., *Corticium* spp., *Phoma* spp., *Rhizoctonia* spp., *Diplodia* spp., *Polymyxa* spp. and *Olpidium* spp.

The present invention is particularly useful for controlling plant diseases caused by Oomycetes which impact diseases affecting soil (seed and root) and foliage plant parts. Typical examples are *Phytophthora infestans* of potato, *Phytophthora nicotianae* of tobacco, *Phytophthora sojae* of soybean, *Plasmopara viticola* of grape, *Bremia lactucae* of lettuce, *Pseudoperonospora cubensis* of the Cucurbitaceae plant family, *Plasmopara halstedii* of sunflower, and plant diseases of corn, cotton, soybean, sorghum, sugar beet and turf caused by *Pythium* spp., the downy mildew fungi, and *Aphanomyces* spp.

In the present invention, ethaboxam can be applied as is; however, it is usually formulated, in advance, by mixing with a solid carrier, liquid carrier, gaseous carrier, surfactant, optionally auxiliaries such as sticking agent, dispersant and stabilizer to form wettable powders, water dispersible granules, suspensible concentrates, dusts, granules, dry flowables, emulsifiable concentrates, aqueous liquid formulations, oil solutions, smoking formulations, aerosols or microcapsule formulations. Ethaboxam is usually contained in an amount of 0.1 to 99%, preferably 0.2 to 90% by weight in the formulation.

Examples of the solid carrier include fine powders and granules of clays such as kaolin, diatomaceous earth, silica, Fubasami clay, bentonite and terra alba; talc; and the other inorganic minerals such as sericite, quartz, sulfur, activated carbon, calcium carbonate and synthetic hydrated silica. Examples of the liquid carrier include water; alcohols such as methanol and ethanol; ketones such as acetone and ethyl methyl ketone; aromatic hydrocarbons such as benzene, toluene, xylene, ethylbenzene and methylnaphthalene; aliphatic hydrocarbons such as hexane, cyclohexane and kerosene; esters such as ethyl acetate and butyl acetate; nitriles such as acetonitrile and butyronitrile; ethers such as dioxane, diisopropyl ether; acid amides such as dimethylformamide and dimethylacetamide; and halogenated hydrocarbons such as dichloroethane, trichloroethylene and carbon tetrachloride.

Examples of the surfactant include alkylsulfate esters, alkylsulfonate salts, alkylarylsulfonate salts, alkylaryl ethers and polyoxyethylenated products thereof, polyoxyethylene glycol ethers, polyvalent alcohol esters and sugar alcohol derivatives.

Examples of other auxiliaries include sticking agents and dispersants, for example, casein, gelatin, polysaccharides (e.g., starch, gum arabic, cellulose derivative, arginic acid), lignin derivatives, bentonite, saccharides, synthetic water soluble polymers (e.g., polyvinyl alcohol, polyvinylpyrrolidone, polyacrylates), PAP (isopropyl acid phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, fatty acids and fatty acid esters.

In the present invention, the application methods of ethaboxam are not restricted and any method can be used, for example, foliar application on plants, soil application treatment methods, and seed treatment slurry and seed-coating applications.

The application on plants can be foliar application to foliage parts or application to tree trunks by spraying, painting and the like.

The soil treatment is accomplished by application to soil or into soil (soil incorporation) or paddy water application by spraying, dripping, drenching, mixing and the like, for example, soil injection treatment (pricking-in hole application with or without mixing with soil), in-furrow treatment (lay-by application with or without mixing with soil, lay-by application into paddy water), soil injection ditch treatment (soil-injection ditch application with or without mixing with soil), row treatment (row application with or without mixing with soil before sowing, row application at growth stage), overall treatment (overall soil application, overall soil-mixing application before sowing), inter-plant treatment, ridge treatment, furrow treatment, nursery bed treatment (nursery bed application to soil or into water), nursery tray treatment (nursery tray application to soil or into water). In particular, in-furrow spray application and soil spray application are preferable. The former is application in water or liquid fertilizer at planting, and spraying into the furrow over the seed or the soil covering the seed just before the seeds are covered. The latter is application in water or liquid fertilizer at planting, and spraying to the soil.

The seed treatment is an application to seed, seed tuber, bulb, plant-cutting and the like, by spray treatment, drip treatment, drench treatment, painting treatment, film-coat treatment, pellet-coat treatment and the like. In particular, a slurry method is preferable, whereby the product is delivered to the seed in a carrier (water) at a predetermined application rate specific to the crop. The slurry may be applied by tumbling seeds while spraying slurry on them or by any other equipment designed to treat seed. Further, in the present application, ethaboxam can be applied to a nutrient solution in water culture.

In the present application, ethaboxam may be applied as a mixture with other fungicides, insecticides, acaricides, nematocides, herbicides, plant growth regulators, fertilizers, soil-improving agents and so on, or it may be applied together with them without mixing.

The application delivery of ethaboxam depends on the weather conditions, type of formulation, application timing, application method, kind of diseases, crop requirements and so on, and it is generally 1 to 500 g, preferably 2 to 200 g per 1000 m$^2$. Emulsifiable concentrate, wettable powder, suspensible concentrate or the like is usually diluted with water and applied. The concentration of ethaboxam is usually 0.0005 to 2%, preferably 0.0005 to 1% by weight. Dust, granule or the like is usually applied without dilution. When ethaboxam is applied to seeds, the application amount of ethaboxam is 0.001 to 25 g, preferably 1.0-10.0 g per 100 KG seed.

EXAMPLES

Hereinafter, the present invention is explained in detail by representative formulation examples and test examples. In the examples, part means part by weight.

Formulation Example 1

Three and three quarters (3.75) parts of ethaboxam, 14 parts of polyoxyethylene styrylphenyl ether, 6 parts of calcium dodecylbenzenesulfonate and 76.25 parts of xylene are mixed well to give an emulsifiable concentrate.

Formulation Example 2

Ten (10) parts of ethaboxam, 35 parts of a mixture of precipitated silica and polyoxyethylene alkyl ether sulfate ammonium (1:1 by weight) and 55 parts of water are mixed and finely wet-pulverized to give a flowable formulation.

Formulation Example 3

Fifteen (15) parts of ethaboxam, 1.5 parts of sorbitan trioleate and 28.5 parts of an aqueous solution containing 2 parts of polyvinyl alcohol, and 45 parts of an aqueous solution containing 0.05 part of xanthan gum and 0.1 part of aluminum magnesium silicate are added thereto, and then, 10 parts of propylene glycol are added thereto and mixed under stirring to give a flowable formulation.

Formulation Example 4

Five (5) parts of ethaboxam, one part of synthetic hydrated silica, 2 parts of calcium ligninsulfonate, 30 parts of bentonite and 62 parts of kaolin clay are mixed and pulverized well, kneaded with water, granulated and dried to give a granular formulation.

Formulation Example 5

Fifty (50) parts of ethaboxam, 3 parts of calcium ligninsulfonate, 2 parts of sodium lauryl sulfate and 45 parts of synthetic hydrated silica are mixed and pulverized well to give a wettable powder formulation.

Formulation Example 6

Three (3) parts of ethaboxam, 85 parts of kaolin clay and 10 parts of talc are mixed and pulverized well to give a dust formulation.

Test Example 1

Ethaboxam, formulated in a flowable concentrate for seed treatment use, was added to water so that the total slurry applied to a specified amount of seed would deliver a designated concentration of ethaboxam per 100 KG seed. The prepared slurry was applied to non-transgenic corn seeds and to transgenic corn seeds having both glyphosate tolerance and rootworm resistance. In a tray, Kimpack (absorbent cellulose wadding, trademark of Kimberly-Clark) was placed and wetted. Each of the corn seed types of each treatment rate was placed on the Kimpack and covered with soil, which is a 1:1 mixture of *Pythium*-infested field soil and sand. After keeping the soil saturated for 14 days at 10° C., the trays were transferred to 18° C. for 11 days. The ratio (%) of emergence of seedlings was observed for investigating the effect for controlling *Pythium* disease. The results are given in Table 1.

TABLE 1

| Concentration of ethaboxam (gai/100 kgseed) | Ratio of sound non-transgenic seeds (%) | Ratio of sound transgenic seeds (%) |
|---|---|---|
| 0.05 | 39 | 57 |
| 0.1 | 41 | 59 |
| 0.5 | 47 | 65 |
| 1.0 | 59 | 67 |

*Pythium* disease was better controlled, and seedling stand establishment was stronger in the transgenic seedlings than non-transgenic seedlings as shown in Table 1.

Test Example 2

Ethaboxam, formulated in a flowable concentrate for seed treatment use, was added to water so that the total slurry applied to a specified amount of seed would deliver a designated concentration. The prepared slurry was applied to non-transgenic corn seeds and transgenic corn seeds having both glyphosate tolerance and rootworm resistance. The treated seeds were planted under field conditions in the early spring when *Pythium* spp. would be most active. Emergence (%) was determined at 7 and 14 DAP and recorded in Table 2.

TABLE 2

| Concentration of ethaboxam (gai/100 kgseed) | Ratio of sound non-transgenic seeds (%) | Ratio of sound transgenic seeds (%) |
|---|---|---|
| 0.05 | 74.5 | 86.25 |
| 0.1 | 78.25 | 85 |
| 0.5 | 76.25 | 89.25 |
| 1.0 | 77.75 | 87.75 |
| 5 | 81 | 86 |
| 10 | 76.25 | 88.5 |

*Pythium* seedling disease of corn was better controlled, and seedling stand establishment was stronger in the transgenic seedlings than non-transgenic seedlings as shown in Table 2 when planted under field conditions.

Test Example 3

The same procedure as Test example 2 was conducted, except that cotton seeds which express *Bacillus thuringiensis* endotoxins and tolerant against glyphosate, were used in place of corn seeds. Disease incited by *Pythium ultimum* is reduced of the transgenic corn. The transgenic cotton source provided higher field stand establishment of seedlings when compared to the non-transgenic cotton. (Table 3).

TABLE 3

| Concentration of ethaboxam (gai/100 kgseed) | Ratio of sound non-transgenic seeds (%) | Ratio of sound transgenic seeds (%) |
|---|---|---|
| 0.05 | 1.75 | 7.5 |
| 0.1 | 6.25 | 6.25 |
| 0.5 | 10.25 | 6 |
| 1.0 | 7 | 14.25 |
| 5 | 9.5 | 8.5 |
| 10 | 6.5 | 17.75 |

What is claimed is:

1. A method for controlling disease in transgenic corn, said method comprising applying 0.001 to 25 g of N-(cyano-2-thienylmethyl)-4-ethyl-2-(ethylamino)-5-thiazolecarboxamide per 100 kg of seed to transgenic corn seeds having both glyphosate tolerance and rootworm resistance.

2. The method according to claim 1, wherein the transgenic corn contains one or more genes expressing a pesticidally active ingredient.

3. The method according to claim 1, wherein the transgenic corn expresses *Bacillus thuringiensis* endotoxins.

4. The method according to claim 1, wherein the disease is caused by an Oomycete fungus.

5. The method according to claim 1, wherein the disease is caused by *Phytophthora* spp. or *Pythium* spp.

6. The method according to claim 1, wherein the disease is caused by *Pythium* spp.

7. The method according to claim 1, wherein the N-(cyano-2-thienylmethyl)-4-ethyl-2-(ethylamino)-5-thiazolecarboxamide is applied to the seeds by seed coating, seed pelleting, or seed treatment slurry.

8. The method according to claim 1, wherein the application amount of N-(cyano-2-thienylmethyl)-4-ethyl-2-(ethylamino)-5-thiazolecarboxamide is 1.0 to 10 g per 100 kg seed.

9. The method according to claim 1, wherein the N-(cyano-2-thienylmethyl)-4-ethyl-2-(ethylamino)-5-thiazolecarboxamide is applied to the seeds by seed treatment slurry.

* * * * *